United States Patent
Hayes

(10) Patent No.: US 9,237,941 B2
(45) Date of Patent: Jan. 19, 2016

(54) ORTHODONTIC APPLIANCE AND SYSTEM

(71) Applicant: Andrew Hayes, O'Fallon, MO (US)

(72) Inventor: Andrew Hayes, O'Fallon, MO (US)

(73) Assignee: Andrew Hayes, Chesterfield, MO (US)

( * ) Notice: Subject to any disclaimer, the term of this patent is extended or adjusted under 35 U.S.C. 154(b) by 0 days.

(21) Appl. No.: 13/713,963

(22) Filed: Dec. 13, 2012

(65) Prior Publication Data

US 2013/0177861 A1 Jul. 11, 2013

Related U.S. Application Data

(60) Provisional application No. 61/579,477, filed on Dec. 22, 2011.

(51) Int. Cl.
*A61C 3/00* (2006.01)
*A61C 7/36* (2006.01)
*A61C 7/20* (2006.01)

(52) U.S. Cl.
CPC .... *A61C 7/36* (2013.01); *A61C 7/20* (2013.01)

(58) Field of Classification Search
CPC .............. A61C 7/00; A61C 7/08; A61C 7/10; A61C 7/12; A61C 7/20; A61C 7/22; A61C 7/36
USPC ............. 433/2, 5, 7, 8, 10, 16, 18, 19, 20, 21, 433/22, 24
See application file for complete search history.

(56) References Cited

U.S. PATENT DOCUMENTS

| 3,508,332 | A | * | 4/1970 | Armstrong | ...................... 433/21 |
| 3,798,773 | A | | 3/1974 | Northcutt | |
| 4,462,800 | A | | 7/1984 | Jones | |
| 4,618,324 | A | | 10/1986 | Nord | |
| 4,708,646 | A | | 11/1987 | Jasper | |
| 4,795,342 | A | | 1/1989 | Jones | |

(Continued)

FOREIGN PATENT DOCUMENTS

EP 1345547 B1 3/2011

OTHER PUBLICATIONS

Collinsdictionary.com. Definition of telescope [retrieved on Dec. 11, 2014]. Retrieved from the Internet: http://www.collinsdictionary.com/dictionary/english/telescoping.*

(Continued)

*Primary Examiner* — Cris L Rodriguez
*Assistant Examiner* — Matthew Saunders
(74) *Attorney, Agent, or Firm* — Andrus Intellectual Property Law, LLP

(57) ABSTRACT

An orthodontic appliance and system are provided for adjusting the relative positions of mandibular and maxillary arches. The orthodontic appliance includes a telescoping assembly including a plurality of telescoping members, and at least a first end member supportably retaining at least a portion of a spring member. The end member is adapted to slidably receive an end of a first telescoping member for selectively interconnection and disconnection therebetween. When interconnected, the spring member extends into an open end of the first telescoping member and is operative to apply spring-force to a second telescoping member. A plurality of interchangeable end members may be provided for use with the telescoping assembly, wherein the different end members have different spring-force delivery attributes. The orthodontic appliance may be installed utilizing an attachment device selectively interconnectable to and disconnectable from orthodontic archwires.

26 Claims, 10 Drawing Sheets

(56) References Cited

U.S. PATENT DOCUMENTS

| | | | |
|---|---|---|---|
| 5,562,445 | A | 10/1996 | DeVincenzo et al. |
| 5,678,990 | A | 10/1997 | Rosenberg |
| 5,738,514 | A | 4/1998 | DeVincenzo et al. |
| 5,829,975 | A | 11/1998 | Gold |
| 5,944,518 | A | 8/1999 | Sabbagh |
| 5,964,588 | A | 10/1999 | Cleary |
| 6,053,730 | A | 4/2000 | Cleary |
| 6,234,792 | B1 | 5/2001 | DeVincenzo |
| 6,244,862 | B1 | 6/2001 | Hanks |
| 6,328,562 | B1 | 12/2001 | Sirney et al. |
| 6,358,046 | B1 | 3/2002 | Brehm et al. |
| 6,361,315 | B1 | 3/2002 | Hanks |
| 6,413,082 | B2 | 7/2002 | Binder |
| 6,558,160 | B2 | 5/2003 | Schnaitter et al. |
| 6,669,474 | B2 | 12/2003 | Vogt |
| 6,884,067 | B2 | 4/2005 | Tuneberg |
| 6,908,306 | B2 | 6/2005 | Bowman et al. |
| 6,964,566 | B2 * | 11/2005 | Sapian ............... 433/18 |
| 6,976,839 | B2 | 12/2005 | Lluch |
| 6,988,888 | B2 | 1/2006 | Cleary |
| 7,070,410 | B2 | 7/2006 | Cacchiotti et al. |
| 7,238,022 | B2 | 7/2007 | Lluch |
| 7,578,671 | B2 | 8/2009 | Corcoran et al. |
| 7,578,672 | B2 | 8/2009 | Sheikh et al. |
| 7,618,257 | B2 | 11/2009 | Lluch |
| 2002/0025502 | A1 | 2/2002 | Williams |
| 2002/0132207 | A1 | 9/2002 | Tuneberg |
| 2003/0064344 | A1 * | 4/2003 | Vazquez ............... 433/19 |
| 2004/0053188 | A1 | 3/2004 | Callabe et al. |
| 2004/0096798 | A1 | 5/2004 | Cleary |
| 2007/0190477 | A1 | 8/2007 | Sheikh et al. |
| 2010/0151402 | A1 | 6/2010 | Williams |
| 2011/0300503 | A1 | 12/2011 | Benvegnu et al. |
| 2012/0135365 | A1 | 5/2012 | Cleary |

OTHER PUBLICATIONS

Collinsdictionary.com. Definition of interconnected [retrieved on Dec. 11, 2014]. Retrieved from the Internet: http://www.collinsdictionary.com/dictionary/english/interconnected.*

International Preliminary Report on Patentability in corresponding PCT Application No. PCT/US2012/069536, mailed Jul. 3, 2014.

Collaborations, Specialty Appliances, Orthodontic Laboratory Services, 4 pages.

Hanks Telescoping Herbst and Miniscope Herbst, Rocoh Orthodontic Appliances, 1 page.

MiniScope Telescoping Herbst, www.americanortho.com, 17 pages.

International Search Report and Written Opinion in corresponding PCT Application No. PCT/US2012/069536, mailed May 21, 2013.

Dentaurum, SUS2, Sabbagh Universal Spring, a new dimension of Class II, improved version Brochure, 2014.

Hanandeh et al., "Evaluating the Effect of Sabbagh Universal Spring During Treatment of Growing Class II Malocclusions", IJO, vol. 21, No. 4, 2010.

Papadopoulos, Moschos, "Orthodontic Treatment of the Class II Noncomplaint Patient: Current Principles and Techniques", Elsevier Health Sciences, 2006, pp. 21-32.

Ritto, A. Korrodi, "Fixed Functional Appliances—A Classification (Updated)", The Orthodontic CYBERjournal, Jun. 2001. http://orthocj.com/2001/06/fixed-functional-appliances-a-classification-updated/.

* cited by examiner

ORTHODONTIC APPLIANCE AND SYSTEM

RELATED APPLICATION INFORMATION

This application claims priority from U.S. Provisional Application Ser. No. 61/579,477, entitled "IMPROVED ORTHODONTIC APPLIANCE AND SYSTEM" filed on Dec. 22, 2011, which is incorporated by reference herein in its entirety.

FIELD OF THE INVENTION

The present invention relates to orthodontic devices employable to realize an increased range of treatment options, while maintaining or even reducing component inventory requirements. More particularly, the invention pertains to orthodontic appliances employable for maxillary/mandibular bite correction and archwire attachment devices advantageously employable therewith.

BACKGROUND OF THE INVENTION

Orthodontic treatment involves the movement of malpositioned teeth to desired positions. During typical treatment, orthodontic brackets are connected to anterior, cuspid, molar, and bicuspid teeth, and an archwire is placed in a slot of each bracket. The archwire guides movement of the brackets and the corresponding teeth to desired positions to correct occlusion. Traditionally, the ends of an archwire have been anchored by appliances known as buccal tubes that are secured to molar teeth (e.g., utilizing bands). More recently, archwire ends are increasingly being secured utilizing buccal tubes bonded directly to molar teeth (e.g., free from use of buccal tubes welded to bands).

Various types of spring devices and elastomeric devices may also be used in orthodontic treatment. The resilient forces of such devices in tension or compression may be used to secure an orthodontic appliance and an interconnected tooth or teeth and correspondingly facilitate movement relative to other orthodontic appliances and an interconnected tooth or teeth. For example, elastomeric rings may be employed as ligatures to secure an archwire in a slot of a bracket. As another example, elongated elastomeric devices (e.g., a chain of interconnected elastomeric ligatures) may be stretched between selected brackets in order to move certain teeth relative to other teeth. Yet other spring devices may be specifically designed to separate adjacent teeth or to rotate a tooth about its long axis.

The orthodontic treatment of some patients includes correction of the alignment of the maxillary dental arch and the mandibular dental arch. For example, certain patients have a condition referred to as a Class II malocclusion wherein the lower dental arch is located an excessive distance rearward of the upper dental arch when the jaws are closed. Other patients may have an opposite condition referred to as a Class III malocclusion wherein the lower dental arch is located forward of the upper dental arch when the jaws are closed.

Orthodontic treatment of Class II and Class III malocclusions typically entails movement of the maxillary dental arch (e.g., teeth comprising the maxillary arch) and/or movement of the mandibular dental arch (e.g., teeth comprising the mandibular arch). For such purposes, an activation force is often applied to teeth of each dental arch by applying a spring force to brackets, archwires or attachments connected to the brackets or archwires. In this manner, the Class II or Class III malocclusion can be corrected as the archwires and brackets are used to move individual teeth to desired positions.

As with all orthodontic treatment regimes, there is a continued focus on addressing Class II and Class III malocclusions in not only a therapeutically effective manner, but also in a manner that yields treatment and orthodontic practice efficiencies. In the latter regard, orthodontic appliances that may be readily installed, adjusted, replaced and removed yield numerous advantages.

SUMMARY OF THE INVENTION

A primary objective of the present invention is to provide improved orthodontic appliances, mounting apparatus and systems that facilitate installation, positioning, adjustment, replacement and removal during a treatment regime.

Another objective is to provide improved orthodontic appliances and mounting apparatus that facilitate the realization of low orthodontic component inventory requirements.

A further objective is to provide improved orthodontic appliances that facilitate selective force application during orthodontic treatment.

Yet another objective is to provide improved orthodontic appliances and mounting apparatus that are relatively easy to use.

To realize one or more of such objectives and additional advantages, an improved orthodontic appliance is provided for adjusting the relative position of teeth comprising the mandibular arch and maxillary arch of a patient. In one embodiment, the orthodontic appliance may include a telescoping assembly that comprises a plurality of telescoping members and two opposing ends. The appliance may further comprise an end member supportably retaining a spring member. The end member may be selectively interconnectable to and disconnectable from an end of a first one of the telescoping members. Upon such selective interconnection and installation of the orthodontic appliance, the spring member may extend into the first telescoping device member, wherein the spring member may be operative to apply a spring force to one of the plurality of telescoping members. In turn, such spring force may be communicated to teeth of maxillary arch and/or mandibular arch of a patient to facilitate desired repositioning of such teeth.

Optionally, the end member may be readily replaced or interchanged with another end member and corresponding, supportably retained spring member having spring attributes that are the same as or different from those of the initially employed spring member (e.g., different spring configurations and/or spring rates characteristics). The interchangeability of end members having spring members with differing attributes may facilitate the progression of orthodontic treatment.

For example, in one embodiment a first end member and corresponding first compression spring member (e.g., a coil spring) may be replaced by a second end member and corresponding second compression spring member (e.g., a coil spring), said second compression spring member being of a length that is greater than a length of the first compression spring member. In turn, for a given common position of the first end member and the second end member, the first compression spring member may be utilized to realize a first degree of teeth repositioning and the second spring member may be utilized to realize a second degree of teeth repositioning. In such embodiments, the first and second end members may be of a common configuration, apart from the lengths of the corresponding first and second spring members, respectively.

In some implementations, an end member may be provided having a tubular portion, wherein at least a portion of the spring member is disposed within the tubular portion. Further, the tubular portion may be adapted to slidably receive an end of the first telescoping member during selective interconnection and disconnection therebetween.

In one approach, the tubular portion of the end member may include an open end and a closed end, wherein a first end of the spring member is interconnected to and extends away from the closed end, with at least a portion of the spring member being disposed within the tubular portion. For example, the spring member may be fixedly interconnected at the closed end of the tubular portion, thereby facilitating manipulation of the end member and spring member as a single unit. In some implementations, the spring member may extend away from the closed end, entirely disposed within the tubular portion.

In some embodiments, a first interconnection member may be interconnected to and extend laterally away from the telescoping assembly, e.g., typically interconnected to and extending laterally away from a first telescoping member at a first end of the telescoping assembly. Such first interconnection member may be provided to facilitate retention of the telescoping assembly and an end member in an interconnected state. Additionally or alternatively, such first interconnection member may be provided for interconnection to an orthodontic device interconnected directly or indirectly to one or more teeth of a patient.

In such embodiments, an end member may include a tubular portion having a sidewall with a slot extending from an open end of the tubular portion along a length thereof, wherein the slot may be sized for passage of the first interconnection member therethrough during selective interconnection and disconnection of the first telescoping member and the end member. The slot may include a retention notch at an end thereof, wherein the first interconnection member may be positioned within the retention notch by advancement through the slot and relative rotation of the tubular portion and first interconnection member. The retention notch may be provided to restrain retractive movement of the first interconnection member when located therein.

In some embodiments, the end member may include an interconnected second interconnection member that extends laterally away from the tubular portion thereof. Such second interconnection member may be provided to facilitate retention of the telescoping assembly and an end member in an interconnected state. Additionally or alternatively, such second interconnection member may be provided for interconnection to an orthodontic device interconnected directly or indirectly to one or more teeth of a patient.

In one arrangement, the second interconnection member may define a laterally extending seat portion having a recess sized to receive at least a portion of the first interconnection member that is interconnected to the first telescoping member. In one approach, the seat portion may define a recess having a configuration that coincides with a peripheral configuration of the first interconnection member.

In some implementations, the first telescoping member and the end member may be selectively interconnectable by axial movement of the first interconnection member along the slot, followed by rotational movement of the first interconnection member into the seat portion. In turn, the first telescoping member and end member may be selectively disconnected by rotational movement of the first interconnection member out of the seat portion and followed by axial movement of the interconnection member along the slot to the open end thereof.

In one arrangement, a first interconnection member may be defined by an eyelet tab and a second interconnection member may be defined by an eyelet seat contoured to matingly receive the eyelet tab. In such arrangements, openings may extend through each of the eyelet tab and the eyelet seat wherein such openings are aligned when the end member is interconnected to the telescoping assembly. As may be appreciated, such openings may be utilized for selective interconnection of the orthodontic appliance to and disconnection of the orthodontic appliance from orthodontic devices interconnected to the maxillary arch and/or mandibular arch of a patient.

In one approach the eyelet tab and the eyelet seat may be provided so that aligned openings thereof are offset from a center axis of the interconnected telescoping assembly and end member at one end of the orthodontic appliance. Optionally, another eyelet tab may be provided at an opposing end of the orthodontic appliance for use in selective interconnection of the orthodontic appliance to and disconnection of the orthodontic appliance from orthodontic devices interconnected to the maxillary arch and/or mandibular arch of a patient. In one embodiment, the additional eyelet tab may be provided so that an opening therethrough is centered upon the above-noted center axis.

In some embodiments, one or a plurality of end members may be provided so that attributes of the corresponding supported spring member(s) is visually indicated. In one approach, a slot may be provided in a tubular portion of each end member that allows for direct visual detection of the corresponding spring member attribute (e.g., a length) through at least a portion of the slot (e.g., a notch portion thereof). Alternatively and/or additionally, a portion of each end member may be at least semi-transparent so as to allow for visual detection of the corresponding spring member attribute therethrough. As may be appreciated, other visual and/or configurational indications may also be utilized.

Improved methods are also provided by the present invention. In one embodiment, a method for providing an orthodontic appliance for adjustment of the relative positions of teeth comprising the mandibular and maxillary arches includes the steps of providing a telescoping assembly, and first interconnecting a first end member to an end of the telescoping assembly. In the latter regard, the first end member may be slidably advanced relative to the telescoping assembly during at least a portion of the first interconnecting step. The method may be provided so that, upon interconnection of the first end member and the telescoping assembly, a first spring member supportably retained by the first end member extends into an open end of the telescoping assembly and is operative to apply a spring-force to at least one of a plurality of telescoping members comprising the telescoping assembly.

In certain implementations, the method may further include the steps of interchanging the first end member with a second end member. The interchanging step may include disconnecting the first end member from the telescoping assembly, and second interconnecting the second end member to the end of the telescoping assembly. During disconnection, the first end member may be slidably retracted relative to the telescoping assembly. The second interconnecting step may entail slidably advancing the second end member relative to the telescoping assembly.

The method may be provided so that, upon interconnection of the second end member and telescoping assembly, a second spring member supportably retained by the second end member extends into an open end of the telescoping assembly and is operative to apply a spring-force to at least one of the plurality of telescoping members. The second spring member and the first spring member may be provided to have different spring attributes (e.g., different spring configurations and/or spring rates).

In another approach, a first interconnection member may be defined by a raised surface portion or post projecting away from the telescoping assembly, and the end member may include a slot for slidably receiving the first interconnection member, wherein the first interconnection member may be retainably located in a notch portion of the slot. In conjunction with such approach, a second interconnection member provided on an end member may be utilized for attachment of the orthodontic appliance directly or indirectly to one or more teeth of a patient. In yet another approach, the first interconnection member may be defined by a hook, eyelet tab or other configuration, wherein an end member may comprise a notched slot, without inclusion of a second interconnection member.

In one approach, the first end member may be provided to include a tubular portion having a side wall with a slot extending from open end of the tubular portion along a length thereof. Further, the telescoping assembly may be provided to have an interconnection member extending laterally away from one of the plurality of telescoping members. In turn, the first interconnecting step may entail positioning an end of the telescoping assembly in the open end of the tubular portion with the first interconnection member located in the slot, advancing the first interconnection member through the slot along an axis of the end member, and rotating at least one of the first end member and the telescoping assembly relative to the other one so as to locate at least a portion of the first interconnection member within a notched portion of the slot.

Further, in some embodiments, the first end member may be provided to have a second interconnection member extending laterally away from tubular portion, wherein the rotating step may comprise positioning at least a portion of the first interconnection member within a seat portion defined by the second interconnection member (e.g., within a recess defined by the second interconnection member). As may be appreciated, the method may be provided so that, when interchanging the first end member with a second end member, the second interconnecting step may comprise advancing, rotating and positioning steps analogous to those noted above in relation to the first interconnecting step.

In another aspect, a method for adjusting the relative positions of mandibular and maxillary arches may be provided, the method may include the steps of providing a telescoping assembly having a plurality of telescoping members, and the interconnecting a first end member to an end of the telescoping assembly. In this regard, upon interconnection of the first end member and the telescoping assembly, a first spring member supportably retained by the first end member may extend into an open end of the telescoping assembly so as to be operative to apply a spring-force to at least one of a plurality of telescoping members. The method may further include the steps of attaching a first end of the telescoping assembly to an archwire interconnected to one of a maxillary arch and mandibular arch and an opposing, second end of the telescoping assembly to an archwire interconnected to the other one of the maxillary arch and mandibular arch, wherein the spring-force of the first spring member may be utilized to provide a first degree of positioning between the maxillary and mandibular arches.

The method may further provide for detachment of at least the first end of the telescoping assembly from the archwire interconnected to the maxillary arch, disconnecting the first end member from the first end of the telescoping assembly, and interconnecting a second end member to the first end of the telescoping assembly. Upon interconnection of the second end member and the telescoping assembly, a second spring member supportably retained by the second end member may be provided to extend into an open end of the telescoping assembly and be operative to apply spring-force to at least one of the plurality of telescoping members. In some arrangements, a second spring member and a first spring member may have differing spring attributes. In turn, the first end or both ends of the telescoping assembly may be attached to the archwire interconnected to the maxillary arch, and if disconnected during the detachment step, the opposing, second end of the telescoping assembly may be attached to the archwire interconnected to the mandibular arch. In turn, the spring-force of the second spring member may be utilized to provide a second degree of relative positioning between the maxillary and mandibular arches.

In various applications, the method for adjusting may further include connecting an orthodontic archwire attachment device to and in a first set position relative to the archwire interconnected to the maxillary arch. In this regard, the first attaching step and the second attaching step may each comprise attaching the first end of the telescoping member to the archwire interconnected to the maxillary arch with the orthodontic archwire attachment device maintained in the first set position relative to the archwire interconnected to the maxillary arch. Relatedly, the method may further include connecting another orthodontic archwire attachment device to and in a second set position relative to the archwire interconnected to the mandibular arch, wherein the first attaching step and second attaching step may each comprise attaching the second end of the telescoping assembly to the archwire interconnected to the mandibular arch with the another archwire attachment device maintained in the second set position relative to the archwire interconnected to the mandibular arch.

In some embodiments, the method may be provided so that the first attaching step includes attachment of an orthodontic archwire attachment device to an interconnection member interconnected to one of the telescoping member and the first end member. Similarly, the second attaching step may include attachment of an orthodontic archwire attachment device to an interconnection member interconnected to one of the telescoping member and the second end member. As may be appreciated, interconnection members may be provided with each of the telescoping member, first end member, and second end member, wherein an interconnection member of the telescoping assembly and an interconnection member of the first end member may be interconnected together, or in tandem, to an orthodontic archwire attachment device, and wherein, an interconnection member of the telescoping assembly and an interconnection member of the second end member may be interconnected together, or in tandem, to an orthodontic archwire attachment device.

To realize additional objectives noted above, an improved archwire attachment device is provided for use in attaching an orthodontic appliance to an archwire. In one embodiment, the archwire attachment device may include a base member having a channel extending therethrough from a first opening to a second opening thereof, and a passageway extending into the base member from an aperture. The channel may be sized for passage of an archwire therethrough from the first opening to a second opening. The passageway may be oriented transverse to and in communication with the channel. In such embodiment, the archwire attachment device may further include a set member selectively advanceable and retractable through the aperture and passageway of the base member in retentive engagement therewith. In turn, the set member may be selectively engageable with an archwire positionable through the channel of the base member for attachment of the archwire attachment device to and in fixed relation relative to an archwire positionable through the channel.

In various embodiments, the orthodontic archwire attachment device may further include an attachment interface member securable to the base member at a port of the base member. The attachment interface member may be adapted for selective interconnection of an orthodontic appliance thereto. By way of example, improved orthodontic appliances described herein may be interconnected for use in adjusting the relative position of teeth comprising the mandibular arch and the maxillary arch of a patient. In one implementation, a port of the base member may include a threaded surface for retentive engagement with a complimentary threaded surface of an orthodontic appliance.

In some arrangements, at least a portion of the passageway of the base member may include a threaded surface and at least a portion of the set member may include a complimentary threaded surface. A first end of the set member may be of a reduced configuration to facilitate retentive engagement with an archwire. A second end of the set member may comprise a recess configured to receive a commonly configured tip of a drive member for use in selective advancement and retraction of the set member in the passageway of the base member. In some embodiments, the set member may be provided so as to be separable from the base member.

In one approach, the passageway and the channel of the base member may adjoin at an angle of +/−5° orthogonal. In implementations including a base member having a port for selective interconnection of an orthodontic appliance thereto, the port may define a center axis therethrough, wherein center axes of the channel, the passageway and the port extend at an angle of +/−5° orthogonal relative to one another. In some implementations, the channel may extend linearly through the base member. In other arrangements, the channel may extend arcuately through the base member.

As may be appreciated, a method is also provided for use in the attachment of an orthodontic appliance to an orthodontic archwire. In one embodiment, the method may include supporting a base member on an orthodontic archwire by positioning the archwire through a channel of the base member from a first opening to a second opening thereof. The method may further include advancing a set member through a passage of the base member to restrainably engage the archwire within the channel after the supporting step, wherein the base member is fixedly positioned relative to the archwire. In turn, the method may further include a step of interconnecting an orthodontic appliance to the base member after the advancing step. As may be appreciated, an orthodontic appliance may be utilized that is of the type described herein for adjusting relative positions of mandibular and maxillary arches.

In one approach, the supporting step may include inserting a free end of the archwire into the first opening of the base member, and moving the base member relative to the archwire to advance the free end of the archwire through the second opening. In turn, the method may include a step of interconnecting the free end of the archwire to an orthodontic device interconnected to at least one tooth in a maxillary arch or mandibular arch, after the supporting step.

In some embodiments, advancement of the set member through the passage of the base member may include advancing the set member from one of a coronal aspect and an apical aspect of the base member. In various implementations, interconnection of an orthodontic appliance to the base member may comprise securement of the orthodontic appliance to a labial aspect of the base member.

In another embodiment, the archwire attachment device may include a base member having first and second channels extending through the base member. The first channel may extend from a first opening of the first channel on a first side of the base member to a second opening of the first channel on a second side of the base member. The second channel may extend from a first opening of the second channel on the first side of the base member to a second opening of the second channel on the second side of the base member. The first and second channels may be sized for passage of an archwire therethrough from the respective first openings to the respective second openings thereof. The base member may also include an appliance side and a mounting side. In this regard, the appliance side may generally comprise a labial aspect of the base member facing the lips and/or cheeks of the patient when the base member is installed on an archwire in the patient's mouth, and the mounting side may generally comprise a lingual aspect of the base member facing the teeth of the patient when the base member is installed on an archwire in the patient's mouth. The first channel may be located closer to the appliance side of the base member than the second channel, and the second channel may be located closer to mounting side of the base member than the first channel. In this regard, the first channel may desirably be utilized for receiving the archwire when the archwire attachment device is to be located on a mandibular arch, and the second channel may desirably be utilized for receiving the archwire when the archwire attachment device is to be located on a maxillary arch. Such desired positioning of the archwire in the first or second channel depending upon the location of the archwire attachment device facilitates the subsequent interconnection of an orthodontic appliance without need to compensate for lateral offset between the mandibular and maxillary arches.

As may be appreciated, a method is also provided for the use of a such a dual channel archwire attachment device in the attachment of an orthodontic appliance to an orthodontic archwire. In one embodiment, the method may include supporting a base member of the attachment device on an orthodontic archwire by positioning the archwire through a first channel formed in the base member when the archwire is to be interconnected to a mandibular arch, or supporting the base member of the attachment device on the orthodontic archwire by positioning the orthodontic archwire through a second channel formed in the base member when the archwire is to be interconnected to a maxillary arch, with the first channel being located closer to an appliance side of the base member than the second channel and the second channel being located closer to a mounting side of the base member than the first channel. The method may further include interconnecting an orthodontic appliance to the base member after the supporting step. Interconnection of the orthodontic appliance may include securing the orthodontic appliance to the appliance side of the base member.

Various appliances, devices and methodologies are provided herein. Such appliances, devices and methodologies may be employed separately and in combination. Numerous additional features and advantages of the present invention will become apparent to those skilled in the art upon consideration of the embodiment descriptions provided hereinbelow.

DETAILED DESCRIPTION

Figure 1:
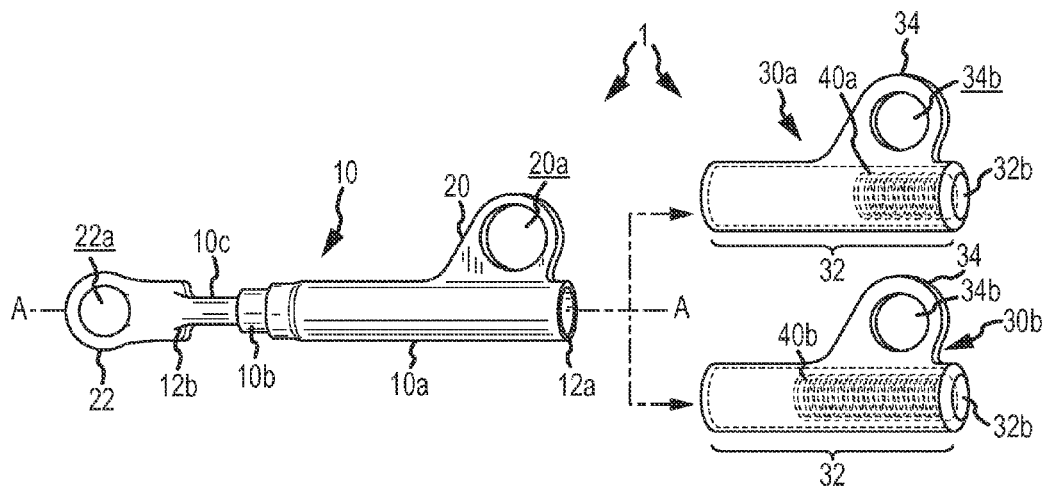
FIG. 1 is a perspective view of one side of an embodiment of an orthodontic appliance that includes a telescoping assembly and a first end member and optional second end member.
Figure 2:
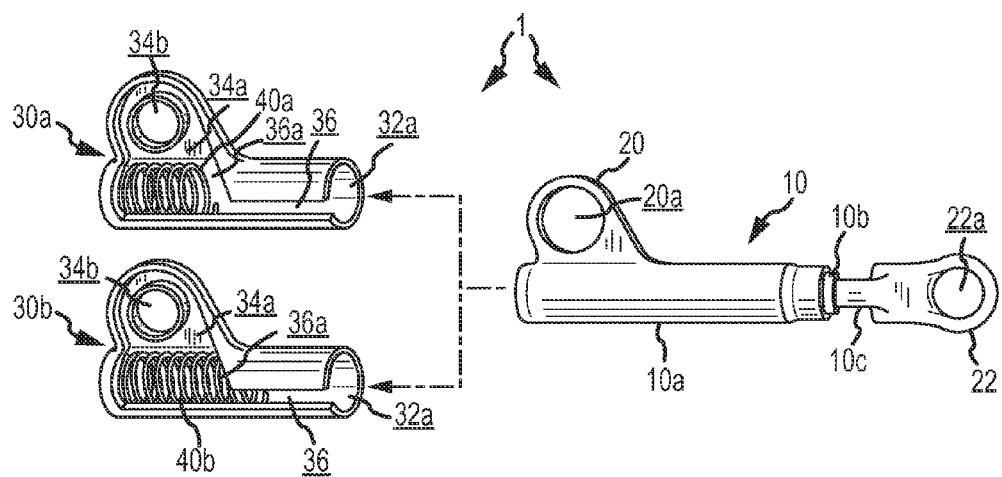
FIG. 2 is a perspective view of another side of the orthodontic appliance embodiment shown in FIG. 1.

FIGS. 1-3 illustrate one embodiment of an orthodontic appliance 1. The orthodontic appliance 1 may include a telescoping assembly 10 having opposing ends 12a, 12b adapted for interconnection to a patient's maxillary arch and mandibular arch. In typical applications, a pair of orthodontic appliances may be installed in a given patient, e.g., one in right side and one in the left side of the patient's oral cavity. The telescoping assembly 10 may comprise a plurality of telescoping members (e.g., two or more). Wherein adjacent ones of the plurality of telescoping members 10 may be provided for sliding engagement. In turn, a total length of the plurality of telescoping members 10 between the opposing ends 12a, 12b thereof may lengthen and shorten as a patient's jaws open and close.

Typically, the telescoping assembly 10 may comprise 2 to 4 members that slide within and/or about adjacent ones thereof, and are restrained from disconnection by interfering portions thereof. In the illustrated embodiment, three telescoping members 10a, 10b and 10c are provided along a common center axis AA. Each of the telescoping members 10a, 10b and 10c is of a cylindrical and tubular configuration. A first telescoping member 10a is sized to slidably receive a second telescoping member 10b, and the second telescoping member 10b is sized to slidably receive a third telescoping member 10c.

To facilitate desired, relative repositioning of a patient's mandibular and maxillary arches, the orthodontic appliance may comprise at least one end member 30a supportably retaining a spring member 40a, wherein the end member 30a may be selectively interconnectable to a first end 12a of the telescoping assembly 10. In turn, spring member 40a may extend into an open end of a first telescoping member 10a to apply a spring force to one of the telescoping members 10 (e.g., a second telescoping member 10b), and such spring force may be communicated during use to teeth of a mandibular and/or maxillary arch to promote desired teeth positioning, as shown schematically in FIGS. 5 and 6.

Optionally, the orthodontic appliance 1 may include a second end member 30b supportably retaining a spring member 40b. The first end member 30a and second end member 30b may be commonly configured for alternate, ready use with the telescoping assembly 10, while the corresponding spring members 40a, 40b may be provided to have different spring attributes. The provision and interchangeability of two or more end members having different spring attributes facilitates a wide range of treatment progression options for orthodontic practitioners.

By way of example, spring members 40a, 40b may be coil springs of a common configuration, with the exception that the spring members 40a, 40b may be of a different length. In that regard, spring member 40b may be of a length that is greater than a length of the spring member 40a. In turn, first end member 30a may be employed so that spring member 40a imparts a correction spring force within a predetermined force range (e.g., a clinically acceptable range) to realize a first degree of teeth repositioning. Then, first end member 30a may be replaced with second end member 30b so that spring member 40 imparts a corrective spring force within the same or another predetermined force range (e.g., clinically acceptable range) to realize a second degree of teeth repositioning.

As shown in FIGS. 1 and 2, end members 30a, 30b may each include a commonly configured tubular portion 32 having an open end 32a and closed end 32b. The spring members 40a, 40b of the end members 30a, 30b, respectively, are retainably supported at closed end 32b of tubular portion 32 and extend towards the open end 32a within the tubular portion 32. In the illustrated example, end members 30a, 30b may be provided so that spring members 40a, 40b, respectively, are fixedly and non-removably positioned at the closed end 32b within the tubular portion 32. As shown, spring members 40a, 40b may be entirely disposed within the tubular portion 32.

Tubular portion 32 of end members 30a, 30b may be configured to slidably receive at least an end portion of the first telescoping member 10a through the open end 32a during interconnection of the telescoping assembly 10 and end member 30a or 30b. In that regard, tubular portion 32 may be of a cylindrical configuration that coincides with the cylindrical configuration of first telescoping member 10a.

In the illustrated embodiment, the first telescoping member 10a may be provided with an interconnection member 20 extending laterally from a side thereof. The first interconnection member 20 may be adapted to facilitate retention of first telescoping member 10a in an interconnected state with end member 30a or 30b and/or to facilitate selective interconnection/disconnection of orthodontic appliance 1 with an orthodontic device interconnected to one or more teeth of a patient.

As shown, end members 30a, 30b may include an interconnection member 34 extending laterally from a side of the tubular portion 32. Interconnection member 34 may be adapted to facilitate selective interconnection/disconnection of orthodontic appliance 1 to one or more teeth of a patient and/or to facilitate retention of first telescoping member 10a in an interconnected state with end member 30a or 30b. In the latter regard, as shown in FIG. 2, interconnection member 34 may include a seat portion 34a having a retention recess for receiving at least a portion of interconnection member 20, as described further hereinbelow.

Figure 5:
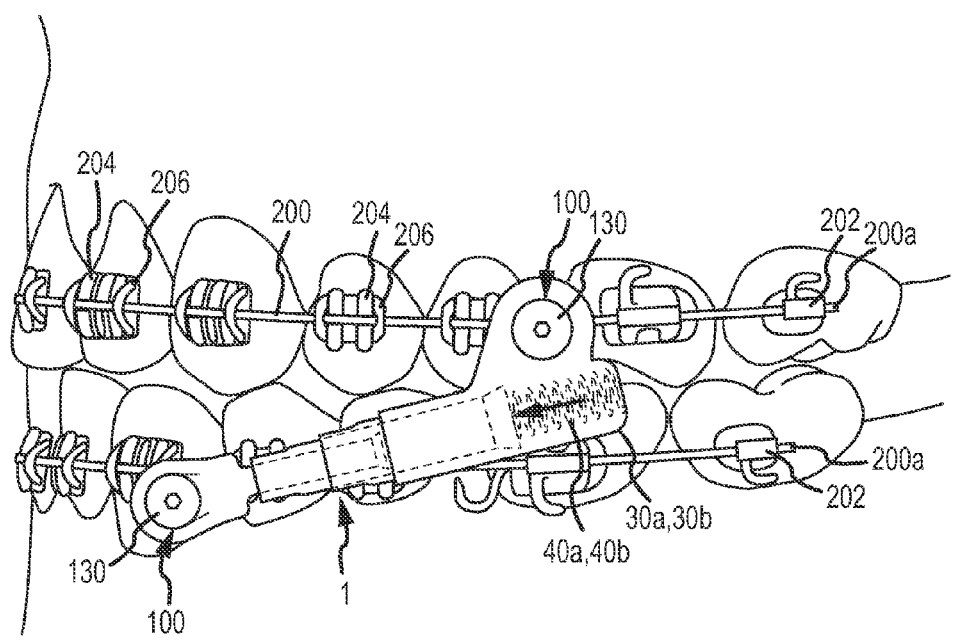
FIG. 5 is an anterior view of the orthodontic appliance embodiment shown in FIG. 1, as installed in a patient's mouth with the patient's maxillary arch and mandibular arch in a first relative position.
Figure 6:
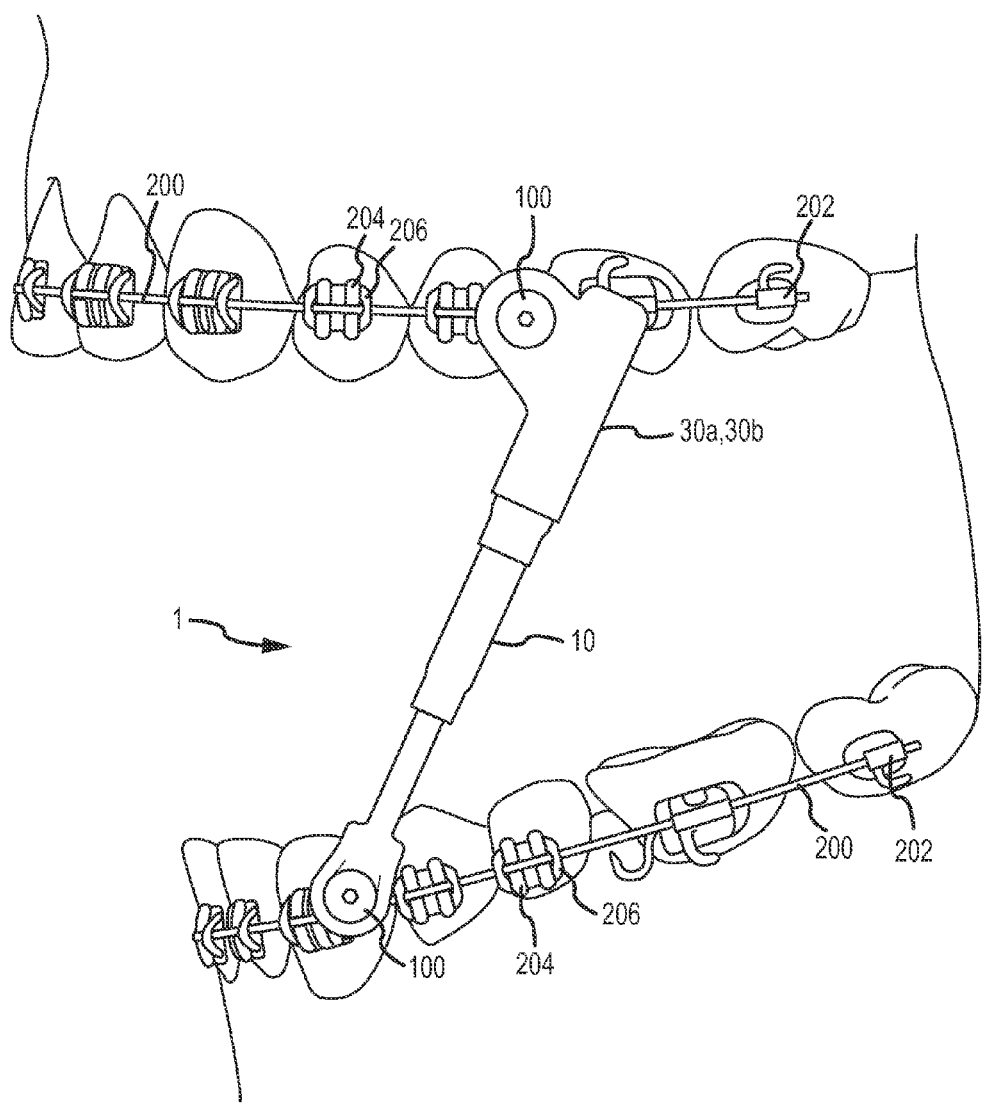
FIG. 6 is an anterior view of the orthodontic appliance embodiment shown in FIG. 1, as installed in FIG. 1, with the patient's maxillary arch and mandibular arch in a second relative position.

In the illustrated embodiment, interconnection members 20 and 34 of first telescoping member 10a and end members 30a, 30b, respectively, may be defined by an eyelet tab and by an eyelet seat, respectively. In this regard, the interconnection member 34, as an eyelet seat, of end members 30a, 30b may be configured to receive a portion of the eyelet tab, therewithin. More particularly, interconnection member 34 of end members 30a, 30b may define a seat portion 34a with a recess having a configuration that coincides with an outer peripheral configuration of interconnection member 20. Further, interconnection member 34 of end members 30a, 30b may include an opening 34b therethrough that is alignable with an opening 20a of interconnection member 20 upon selective interconnection of the telescoping assembly 10 and end member 30a or 30b. Such aligned openings 34b, 20a may receive an orthodontic device therethrough for interconnecting orthodontic appliance 1 to one or more teeth of a patient, as shown in FIGS. 5 and 6, and further described below. Optionally, an interconnection member 22 may be provided at the second end 12b of telescoping assembly 10 for selective interconnection to and disconnection from an orthodontic device provided for interconnecting orthodontic appliance 1 to one or more teeth of a patient, as shown in FIGS. 5 and 6, and further described below. In the illustrated embodiment, interconnection member 22 may be optionally defined by an eyelet tab 22c on third telescoping member 10c and may include an opening 22a therethrough.

In one embodiment, end members 30a, 30b may comprise a polymer material, e.g., a semi-transparent, thermoplastic material that may be vacuum-molded (e.g., an acrylic material) to a configuration corresponding with at least a portion of first telescoping member 10a. In another approach, the end members 30a, 30b may comprise a metal (e.g., stainless steel) appropriate for orthodontic use and having a configuration corresponding with at least a portion of first telescoping member 10a. Relatedly, telescoping assembly 10 may typically comprise a metal (e.g., stainless steel) appropriate for orthodontic use.

Figure 3A:
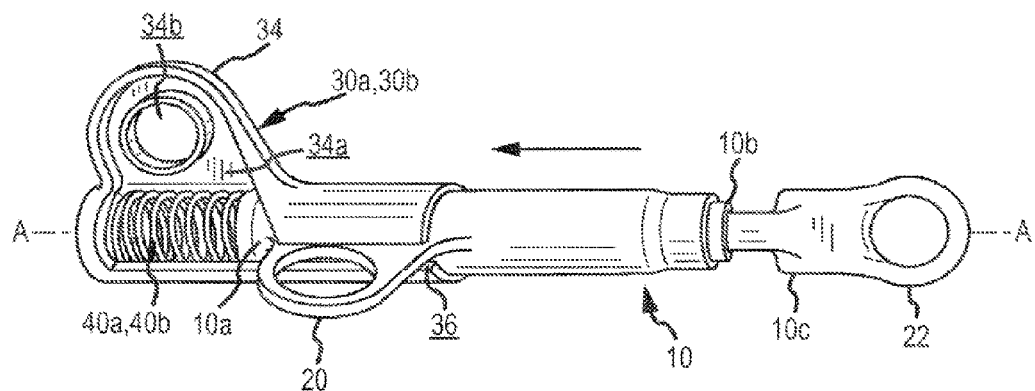
FIG. 3A is a perspective side view of the orthodontic appliance embodiment of FIG. 2, illustrating the interconnection member of the first telescoping member positioned within the slot of the end member.
Figure 3B:
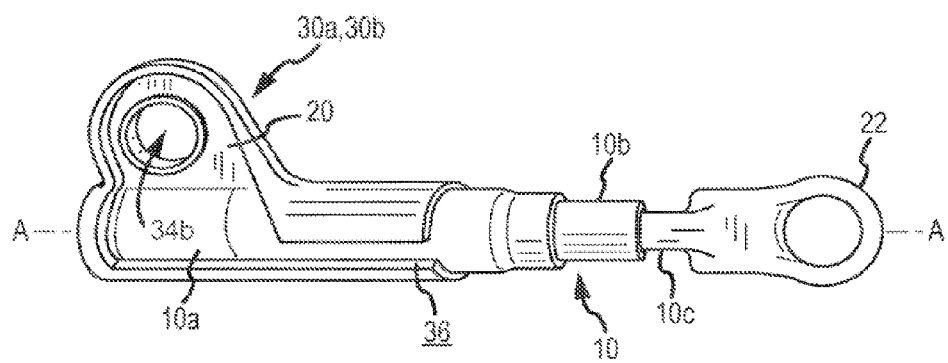
FIG. 3B is a perspective side view of the orthodontic appliance embodiment of FIG. 2, illustrating the interconnection member of the first telescoping member positioned within the retention notch of the end member.

Interconnection of telescoping assembly 10 to end members 30a, 30b will now be described with reference to FIG. 2, FIG. 3A and FIG. 3B. In this regard, it is initially noted that a sidewall of tubular portion 32 of end members 30a, 30b may be provided with a slot 36 that extends from the open end 32a along a length of the tubular portion 32. The slot 36 is in open communication with the open area within tubular portion 32, wherein a key-way configuration may be defined. As shown, the slot 36 terminates at a retention notch 36a, wherein the slot 36 and retention notch 36a thereof are sized to receive a base portion of interconnection member 20 therethrough.

More particularly, the slot 36 may be sized so that the end of the first telescoping member 10a and/or end member 30a or 30b may be positioned to align interconnection member 20 with slot 36 at the open end 32a of tubular portion 32. Then, the end of first telescoping member 10a may be slidably received in slot 36 as the first tubular member 10a is advanced into, within and along tubular portion 32 towards closed end 32b, as shown in FIG. 3A. In turn, upon advancement of first telescoping member 10a to retention notch 36a, the first telescoping member 10a and/or end member 30a, 30b may be rotated relative to one another so as to retainably position interconnect member 20 within the retention notch 36a, as shown in FIG. 3B. Concomitantly, the interconnection member 20 may be seated within the seat portion 34a of interconnection member 34. The interconnected telescoping assembly 10 and end member 30a, 30b may then be selectively positioned in a patient's mouth as described below.

As may be appreciated, disconnection of telescoping assembly 10 from end member 30a, 30b may occur in a reverse manner from that described above. For example, such disconnection may occur when a practitioner elects to interchange end member 30a with end member 30b, whereupon interconnection/disconnection of end member 30b to/from telescoping assembly 10 may also be carried out as described. Such alternate use of end members 30a, 30b may be repeated any number of times during a given treatment regime. Further in that regard, it should be noted that any number of end members having different corresponding spring characteristics may be provided, wherein each of such end members are commonly configured for interchangeable use with a given telescoping assembly 10.

As noted above, telescoping assembly 10 and end member 30a, 30b may be installed as an interconnected unit in a patient's mouth via selective interconnection with orthodontic devices interconnected to one or more teeth of a patient's maxillary jaw and one or more teeth of a patient's mandibular jaw. In this regard, the orthodontic devices may be adapted for direct or indirect interconnection with one or more teeth of a patient. Typically, such orthodontic devices may be adapted for selective interconnection to and disconnection from other orthodontic componentry utilized in connection with a given orthodontic treatment regime. For example, such orthodontic devices may include devices interconnectable to bands and/or brackets attached to a patient's teeth, and/or to archwires utilized with orthodontic brackets.

In the embodiment shown in FIGS. 5 and 6, an orthodontic appliance attachment device 100 is illustrated which allows for selective interconnection of an interconnected unit of telescoping assembly 10 and end member 30a or 30b at a continuum of locations along archwires 200. The archwires 200 may be interconnected to molar teeth or other teeth of a patient via buccal tubes 202 or brackets. The archwires 200 may be provided to engage brackets 204 interconnected to a patient's teeth, wherein ligatures 206 may be employed to maintain a desired interface between archwires 200 and brackets 204. Of note, attachment device 100 may be provided to yield enhanced positioning/anchoring options for orthodontic appliances, including in particular, the embodiment of orthodontic appliance 1 described above.

Figure 4A:
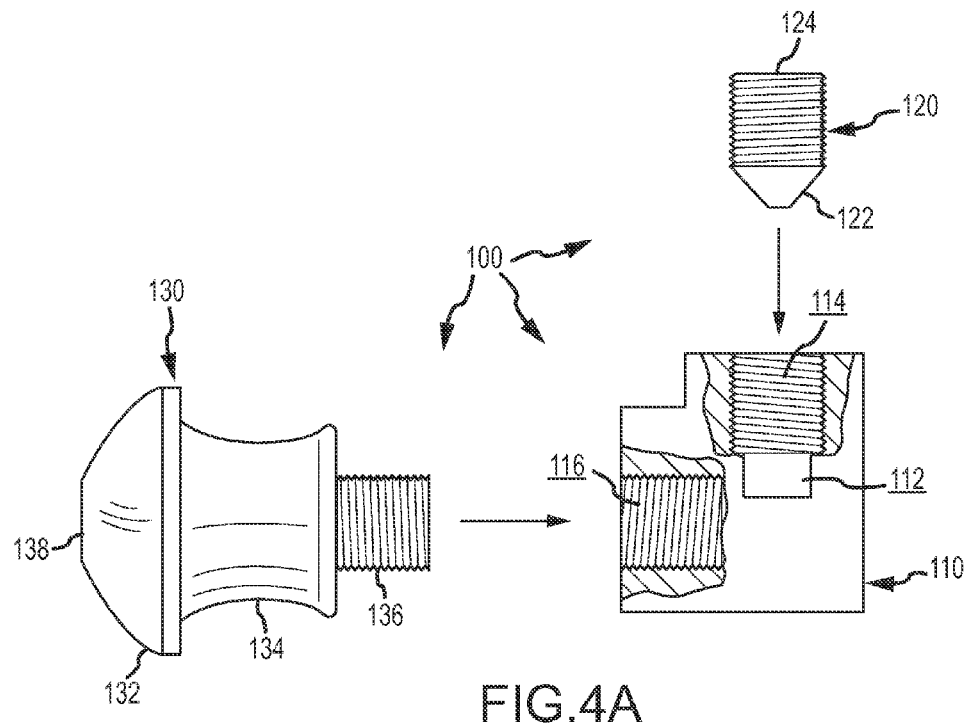
FIG. 4A is a partial cut-away view of an attachment device employable for attachment of orthodontic appliances to orthodontic archwires, including attachment of the orthodontic appliance embodiment of FIG. 1.
Figure 4B:
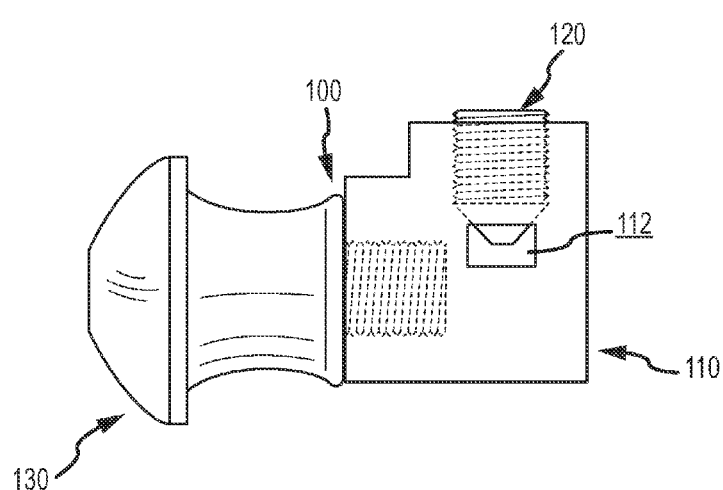
FIG. 4B is a plan end view of an attachment device employable for attachment of orthodontic appliances to orthodontic archwires, including attachment of the orthodontic appliance embodiment of FIG. 1.
Figure 4C:
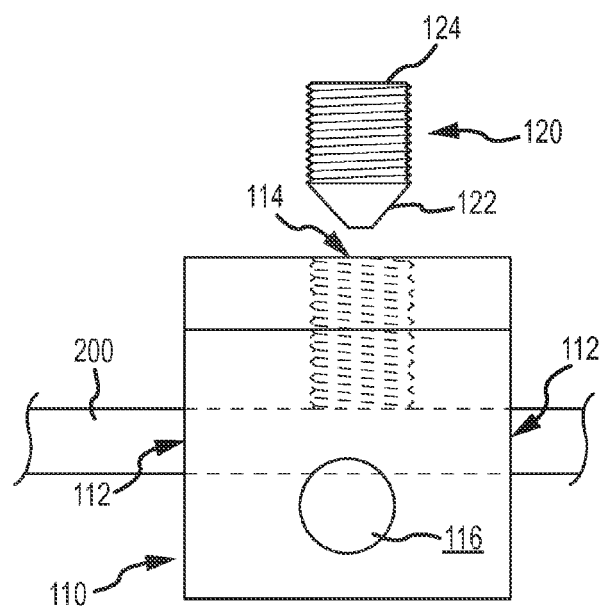
FIG. 4C is a front view of a base member and set member of the attachment device embodiment of FIGS. 4A and 4B located on an orthodontic archwire.

In this regard, reference is now made to FIGS. 4A, 4B and 4C which illustrate an embodiment of an improved archwire attachment device 100. Attachment device 100 may include a base member 110, a set member 120, and an attachment interface member 130. The base member 110 may comprise a channel 112 extending therethrough, from a first side to an opposing, second side of base member 110. The channel 112 may be sized for passage of an archwire therethrough, e.g., archwire 200 shown in FIGS. 5 and 6. More particularly, channel 112 may be provided so that an end of an archwire may be inserted into one end of the channel 112 on one side of the base member 110 (e.g., the first side), and advanced through the channel 112 to exit the channel 112 on the other side of the base member 110 (e.g., the second side), wherein the base member 110 may then be slidably and supportably positioned along the archwire. In various arrangements, the channel 112 may be provided to extend linearly or slightly arcuately through the base member 110.

The base member 110 may further include a passageway 114 that is transverse to and in open communication with channel 112. For example, passageway 114 may transversely adjoin channel 112, wherein a center axis of passageway 114 and a center axis of channel 112 are orthogonal or within +/−5° of being orthogonal. As illustrated, passageway 114 may extend from a third side of base member 110 to channel 112. The passageway 114 may be provided for selective advancement/retraction of set member 120 therewithin, wherein set member 120 may be selectively positioned so that a first end 122 thereof may protrude into the channel 112 to restrainably engage an archwire positioned through the channel 112 such that base member 110 is fixedly positioned, or anchored, relative to the archwire. To facilitate retention engagement, passageway 114 may comprise internal threading and set member 120 may comprise complimentary, external threading, wherein set member 120 may be rotatively advanced or retracted to a desired "set" position. In turn, a second end 124 of set member 120 may be adapted for driven advancement/retraction (e.g., via a recess configured to receive a commonly configured drive tip). As shown, the first end 122 of set member 120 may be tapered (e.g., to define a frusto-conical end), so as to facilitate retentive interface with an archwire positioned through channel 112.

Base member 110 may further include a port 116 for selective receipt and interconnection of attachment interface member 130 therewithin. In this regard, the attachment interface 130 may be of a type that is compatible for use with orthodontic appliance 1. By way of example, the attachment interface member 130 may comprise a rounded head portion 132, a reduced neck portion 134 having a convexly-configured outer surface to define a saddle-like retention ring, and an end portion 136 adapted for retentive securement within the port 116 of base member 110. In this regard, the end portion 136 and neck portion 134 may be sized for positioning through the openings 20a and 34b of first interconnection member 20 and second interconnection member 34 of the telescoping assembly 10 and end member 30a, 30b, respectively. Further, the head portion 132 may be sized to be larger than the openings 20a and 34a. In turn, upon interconnection of telescoping assembly 10 and an end member 30a or 30b, the aligned openings 20a and 34b may be advanced over the end portion 136, wherein the first interconnection member 20 and second interconnection member 34 are supported about the neck portion 134 of the attachment interface member 130. Then, the attachment interface member 130 may be interconnected to the base member 110, wherein the first interconnection member 20 and second interconnection member 34 may be restrainably positioned between the head portion 132 of the attachment interface member 130 and the base member 110.

In one approach, base member 110, set member 120 and/or attachment interface member 130 may comprise a metal appropriate for orthodontic use. For example, a stainless steel material may be used.

An example of one approach for use of orthodontic appliance 1 and archwire attachment device 100 will now be described. With reference to FIG. 5, a free end 200a of an archwire 200 may be disconnected from one or more orthodontic devices utilized to anchor the end 200a of archwire 200 (e.g., one or more buccal tubes 202 and/or orthodontic brackets). The free end 200a of the archwire 200 may be inserted into and advanced through the channel 112 of the base member 110 of attachment device 100 from a first opening to a second opening thereof, as shown in FIG. 4C. The base member 110 may be advanced along archwire 200 to or near a desired anchor location, with the passageway 114 oriented in a coronal aspect or apical aspect, as desired. The end 200a of archwire 200 may then be resecured to one or more orthodontic devices utilized to anchor the end 200a of the archwire 200. Then, with the base member 110 located at the desired anchor location along archwire 200, with the passageway 114 oriented in a desired position, set member 124 may be advanced into passageway 114 and into retentive engagement with archwire 200. Such interconnection of a base member 110 may be carried out in relation to both the maxillary arch and the mandibular arch. As shown in FIGS. 5 and 6, archwire attachment devices 100 may be located at locations corresponding with desired anchor locations of an orthodontic appliance 1.

To position an orthodontic appliance 1, attachment interface member 130 may be located through the aligned openings 20a and 34a of first interconnection member 20 and second interconnection member 34 of the telescoping assembly 10 and end member 30a, 30b, respectively, wherein such componentry is supportably located about the neck portion 134. In turn, the attachment interface member 130 may be selectively secured to the base member 110 located on a maxillary archwire as described above. An analogous procedure may be utilized for interconnection of interconnection member 22 to an archwire attachment device 100 interconnected to archwire interconnected to the mandibular arch as illustrated. After installation of the appliance 1, end members 30a, 30b may be interchanged as described hereinabove. Such interchange may be carried out via detachment of an interface member 130, without detaching the base member 110 from the archwire 200.

Referring now to FIGS. 8A-8F another embodiment of an improved archwire attachment device 800 is illustrated. Attachment device 800 may include a base member 810 and an attachment interface member 830. The base member 810 may include first and second channels 812A, 812B extending therethrough, from a first side 810A to an opposing, second side 810B of base member 810. In this regard, archwire attachment device 800 may be referred to herein as dual channel archwire attachment device 800. Channels 812A, 812B may extend substantially parallel with one another through the base member 810 between an appliance side 810C and a mounting side 810D of base member 810. The appliance side 810C may generally be the side of the base member 810 to which an orthodontic appliance is attachable and the mounting side 810D may generally be the side facing the teeth when the base member 810 is mounted on an archwire installed on the mandibular arch or maxillary arch of a patient.

Each channel 812A, 812B may be sized for passage of an archwire therethrough, e.g., archwire 200 shown in FIGS. 5 and 6. More particularly, each channel 812A, 812B may be provided so that an end of an archwire may be inserted into one end of either channel 812A, 812B on one side of the base member 810 (e.g., the first side), and advanced through the respective channel 812A, 812B to exit the respective channel 812A, 812B on the other side of the base member 810 (e.g., the second side), wherein the base member 810 may then be slidably and supportably positioned along the archwire. In various arrangements, the channels 812A, 812B may be provided to extend linearly or slightly arcuately through the base member 810. Further, the channels 812A, 812B may be provided with a rectangular cross-section for receipt of an archwire having a corresponding rectangular cross-section. In this regard, the rectangular cross-section archwire and rectangular cross-section channels 812A, 812B cooperate to restrict rotation of the base member 810 relative to the archwire.

Base member 810 may further include a port 816 for selective receipt and interconnection of attachment interface member 830 therewithin. Port 816 may extend from an opening on the attachment side 810C of base member 810 toward an opening on the mounting side 810D of base member 810. In some embodiments, port 816 may not extend all the way through base member 810 to an opening on the mounting side 810D and may instead only be open on the appliance side 810C. The attachment interface 830 may be of a type that is compatible for use with an orthodontic appliance such as described herein. By way of example, the attachment interface member 830 may comprise a rounded head portion 832, a reduced neck portion 834 having a convexly-configured outer surface to define a saddle-like retention ring, and an end portion 836 adapted for retentive securement within the port 816 of base member 810. In this regard, the end portion 836 and neck portion 834 may be sized for positioning through the openings 20a and 34b of first interconnection member 20 and second interconnection member 34 of the telescoping assembly 10 and end member 30a, 30b, respectively, of orthodontic appliance 1. Further, the head portion 832 may be sized to be larger than the openings 20a and 34a. In turn, upon interconnection of telescoping assembly 10 and an end member 30a or 30b, the aligned openings 20a and 34b may be advanced over the end portion 836, wherein the first interconnection member 20 and second interconnection member 34 are supported about the neck portion 834 of the attachment interface member 830. Then, the attachment interface member 830 may be interconnected to the base member 810, wherein the first interconnection member 20 and second interconnection member 34 may be restrainably positioned between the head portion 832 of the attachment interface member 830 and the base member 810.

One example of the configuration of attachment interface member 830 that is particularly suited for use with an orthodontic appliance as described herein has been provided. Attachment interface member 830 may also be configured for use with orthodontic appliances other than those described herein.

In one approach, base member 810 and attachment interface member 830 may comprise a metal appropriate for orthodontic use. For example, a stainless steel material may be used.

Figure 8A:
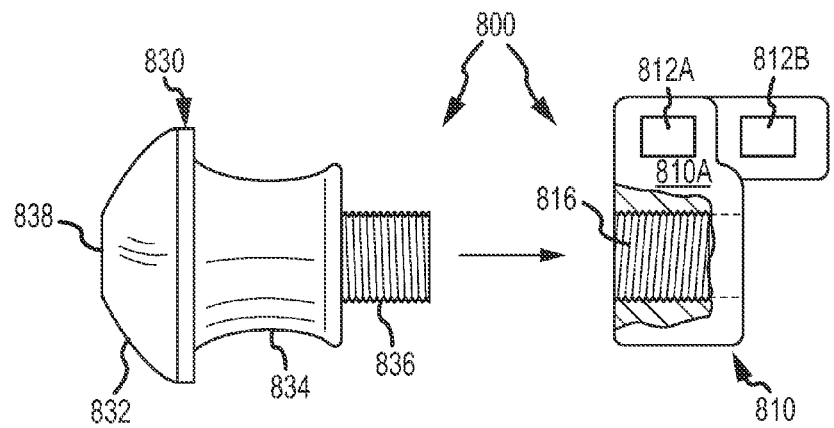
FIG. 8A is a partial cut-away view of another embodiment of an attachment device employable for attachment of orthodontic appliances to orthodontic archwires, including attachment of the orthodontic appliance embodiments as shown in FIG. 2 and FIG. 7.
Figure 8B:
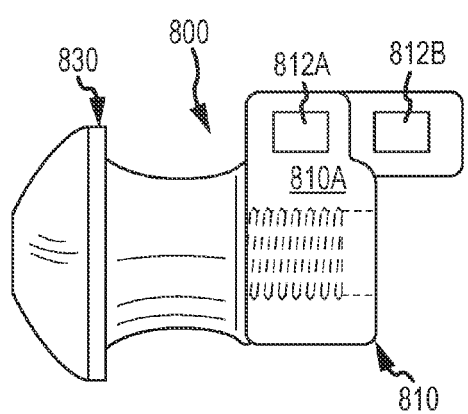
FIG. 8B is a plan end view of another embodiment of an attachment device employable for attachment of orthodontic appliances to orthodontic archwires, including attachment of the orthodontic appliance embodiments as shown in FIG. 2 and FIG. 7.
Figure 8C:
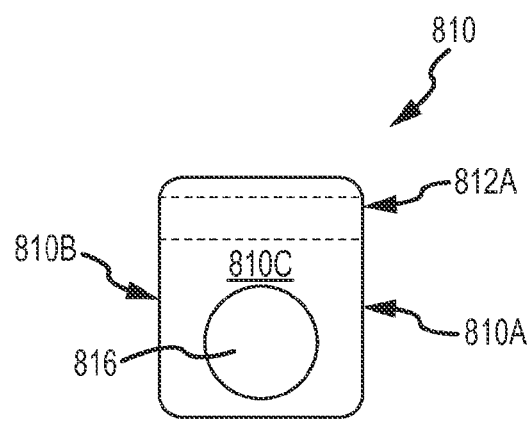
FIG. 8C is a front view of a base member of the attachment device embodiment as depicted in FIGS. 8A and 8B.
Figure 8D:
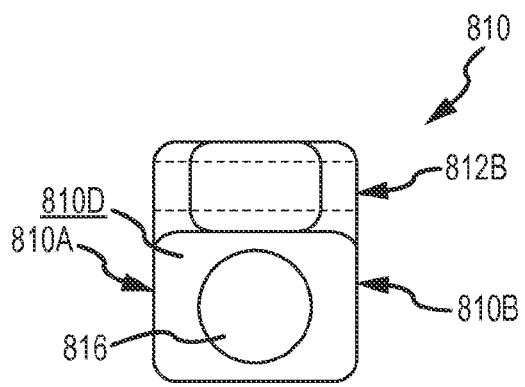
FIG. 8D is a rear view of the base member of the attachment device embodiment as depicted in FIGS. 8A and 8B.
Figure 8E:
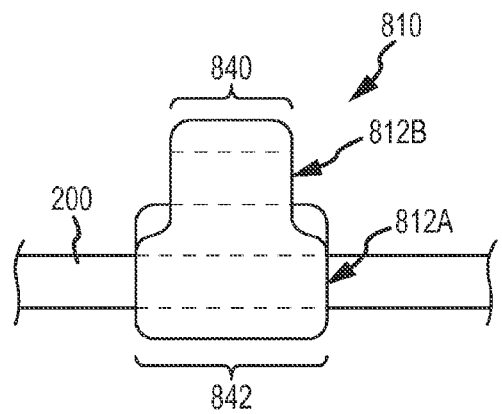
FIG. 8E is a top view of the base member of the attachment device embodiment of FIGS. 8A and 8B located on an orthodontic archwire interconnected to a mandibular arch.
Figure 8F:
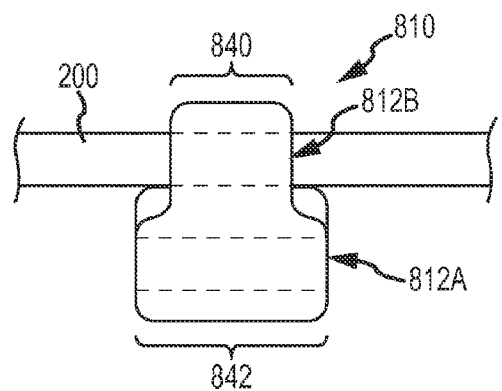
FIG. 8F is a top view of the base member of the attachment device embodiment of FIGS. 8A and 8B located on an orthodontic archwire interconnected to a maxillary arch.

The archwire attachment device 800 of FIGS. 8A-8F includes a number of features that are similar to those included in the archwire attachment device 100 of FIGS. 4A-4C, but archwire attachment device 800 is differently configured in several respects. For example, instead of having a single channel that receives the archwire regardless of whether the base member is located on an archwire interconnected to a maxillary arch or a mandibular arch, the archwire attachment device 800 includes two channels 812A, 812B, each of which is sized for passage of an archwire 200. In this regard, as illustrated in FIG. 8E, the first channel 812A receives the archwire 200 when the attachment device 800 is located on an archwire 200 interconnected to a mandibular arch, and as illustrated in FIG. 8F, the second channel 812B receives the archwire 200 when the attachment device 800 is located on an archwire 200 interconnected to a maxillary arch. In this regard, the first channel 812A may be referred to herein as the mandibular channel 812A, and the second channel 812B may be referred to herein as the maxillary channel 812B. Of note, mandibular channel 812A is nearer to the appliance side 810C of the base member 810 than is maxillary channel 812B which is closer to the mounting side 810D of the base member 810. Having separate mandibular and maxillary channels 812A, 812B with the mandibular channel 812A being closer to the side of the base member 830 on which the attachment interface member 830 is received (the appliance side 810C) facilitates interconnection of an orthodontic appliance to the mandibular and maxillary arches without requiring the use of different length attachment interface members 830 in order to compensate for relative lateral offset between where the orthodontic appliance is interconnected to the mandibular arch and where it is interconnected to the maxillary arch.

Additionally, the attachment device 800 of FIGS. 8A-8F does not include the set member 120 and passageway 114 included in the attachment device 100 of FIGS. 4A-4C whereby set member 120 may restrainably engage the archwire 200 to fix the position of the base member 110 of the attachment device 100 relative to the archwire 200. Instead, the base member 810 of the attachment device 800 is free to slide on the archwire 200. Sliding of base member 810 on the archwire 200 may be restrained within a limited range by contact between base member 810 and brackets attaching the archwire 200 to teeth that are forward and rearward of the base member 810. In this regard, base member 810 may include a protruding portion 840 on the mounting side 810D thereof that is more narrow in width than a main portion 842 of base member 810. The more narrow protruding portion 840 faces the teeth when installed on an archwire 200 and may be less likely to come into contact with the teeth when sliding on the archwire 200 due to its more narrow width than if protruding portion 840 were of the same width as the main portion 842.

One approach of using an orthodontic appliance 1 and dual channel archwire attachment device 800 is similar to the approach as described herein in relation to the use of orthodontic appliance 1 and single channel archwire attachment device 100. In this regard, a free end 200a of an archwire 200 may be disconnected from one or more orthodontic devices utilized to anchor the end 200a of archwire 200 (e.g., one or more buccal tubes 202 and/or orthodontic brackets). If the archwire 200 is interconnected to a mandibular arch, the free end 200a of the archwire 200 may be inserted into and advanced through the first channel 812A of the base member 810 of attachment device 800 from a first opening to a second opening of the first channel 812A. If the archwire 200 is interconnected to a maxillary arch, the free end 200a of the archwire 200 may be inserted into and advanced through the second channel 812B of the base member 810 of attachment device 800 from a first opening to a second opening of the second channel 812B. The base member 810 may be advanced along archwire 200 to or near a desired anchor location (e.g., distal to the canine for the mandibular arch and mesial to the first molar for the maxillary arch). The end 200a of archwire 200 may then be resecured to one or more orthodontic devices utilized to anchor the end 200a of the archwire 200. Such interconnection of dual channel base members 810 may be carried out in relation to both the maxillary arch and the mandibular arch.

To position an orthodontic appliance 1, attachment interface member 830 may be located through the aligned openings 20a and 34a of first interconnection member 20 and second interconnection member 34 of the telescoping assembly 10 and end member 30a, 30b, respectively, wherein such componentry is supportably located about the neck portion 834. In turn, the attachment interface member 830 may be selectively secured to the base member 810 located on a maxillary archwire. An analogous procedure may be utilized for interconnection of interconnection member 22 to an archwire attachment device 800 interconnected to archwire interconnected to the mandibular arch. After installation of the appliance 1, end members 30a, 30b may be interchanged as described hereinabove. Such interchange may be carried out via detachment of an interface member 830, without detaching the base member 810 from the archwire 200.

Figure 7:
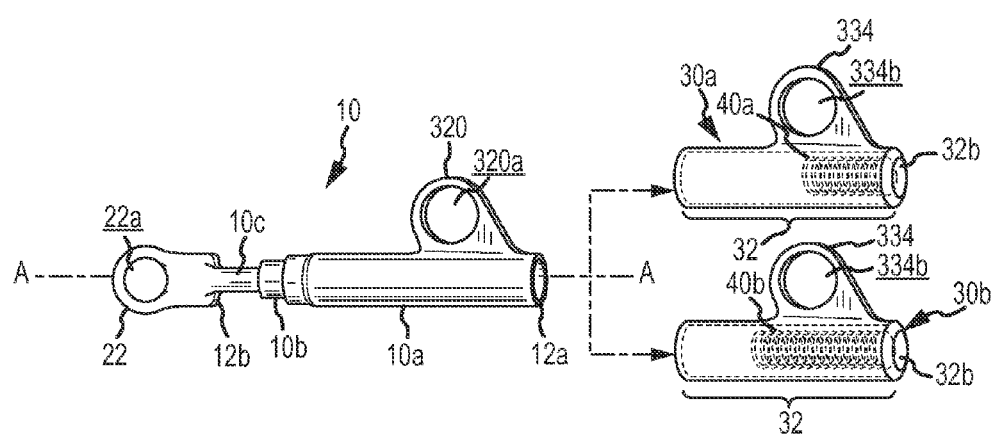
FIG. 7 is a perspective view of one side of another embodiment of an orthodontic appliance that includes a telescoping assembly and a first end member and optional second end member.

The foregoing embodiment descriptions have been presented for purposes of illustration. The descriptions are not intended to limit the invention to specific configurations. Consequently, variations and modifications commensurate with the above teachings, and skill and knowledge of the relevant art, are within the scope of the present invention. For example, FIG. 7 illustrates a modified version of the orthodontic appliance embodiment of FIG. 1. In the FIG. 7 embodiment, a first interconnection member 320 is exemplarily an eyelet tab 320 and a second interconnection member 334 is exemplarily an eyelet seat 334, wherein corresponding openings 320a and 334b may be located/aligned at a greater distance from the first end 12a of the telescoping assembly (e.g., closer to the second end 12b of the telescoping assembly) than openings 20a and 34b of the FIG. 1 embodiment. Such an arrangement may provide advantages in some implementations (e.g., decrease of the interarch distance needed for the appliance, increase of potential case use applications, etc.).

The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. An orthodontic appliance for adjusting the relative positions of teeth comprising mandibular and maxillary arches, comprising:
a telescoping assembly having two opposing ends and a plurality of telescoping members;
a first end member supportably retaining at least a portion of a first spring member, said first end member being adapted to slidably receive an end of a first telescoping member of said plurality of telescoping members at one of said opposing ends for selective interconnection and disconnection therebetween, wherein when said first end member is interconnected to said end of the first telescoping member said first spring member extends into an open end of the first telescoping member and is operative to apply a spring-force to a second telescoping member of said plurality of telescoping members; and
a second end member supportably retaining at least a portion of a second spring member, said second end member being adapted to slidably receive the end of the first telescoping member at one of said opposing ends for selective interconnection and disconnection therebetween, wherein when said second end member is interconnected to said end of the first telescoping member said second spring member extends into an open end of the first telescoping member and is operative to apply a spring-force to the second telescoping member, and wherein said first spring member and said second spring member have different spring attributes wherein the first end member and the second end member are selectively and fixedly securable to the first telescoping member.

2. An orthodontic appliance as recited in claim 1, said first end member comprising:
a tubular portion, wherein said first spring member is at least partially disposed within said tubular portion.

3. An orthodontic appliance as recited in claim 2, said tubular portion comprising: an open end and a closed end, wherein a first end of said first spring member is interconnected to said end members at said closed end of the tubular portion thereof, and wherein said spring member extends away from said closed end within said tubular portion.

4. An orthodontic appliance as recited in claim 3, said spring member being fixedly and unremovably interconnected at said closed end of said tubular portion.

5. An orthodontic appliance as recited in claim 3, said spring member being entirely disposed within said tubular portion.

6. An orthodontic appliance as recited in claim 1, wherein said first end member comprises a tubular portion and said second end member comprises a tubular portion, wherein said tubular portion of the first end member and the tubular portion of the second end member are of a substantially common configuration.

7. An orthodontic appliance as recited in claim 1, said first telescoping member having a first interconnection member extending laterally away therefrom, and said end members having a tubular portion with a slot extending through a sidewall thereof from an open end of the tubular portion along a length thereof, wherein said slot is sized for passage of the first interconnection member therethrough during selective interconnection and disconnection of the first telescoping member and the end members.

8. An orthodontic appliance as recited in claim 7, further comprising a retention notch extending from the slot through the tubular portion of the end members, the retention notch engages the first interconnection member and restricts relative axial movement of the first interconnection member and the end members.

9. An orthodontic appliance as recited in claim 7, said end members further having a second interconnection member that includes a seat portion extending laterally away from said tubular portion and sized to receive at least a portion of the first interconnection member.

10. An orthodontic appliance for adjusting the relative positions of teeth comprising mandibular and maxillary arches comprising: a telescoping assembly having two opposing ends and a plurality of telescoping members including a first telescoping member having a first interconnection member extending laterally away therefrom; and a first end member supportably retaining at least a portion of a first spring member, said first end member having a tubular portion with a slot extending through a sidewall thereof from an open end of the tubular portion along a length thereof, wherein said slot is sized for passage of the first interconnection member therethrough during selective interconnection and disconnection of the first telescoping member and the first end member, said first end member being adapted to slidably receive an end of the first telescoping member at one of said opposing ends for selective interconnection and disconnection therebetween, wherein when said first end member is interconnected to said end of the first telescoping member said first spring member extends into an open end of the first telescoping member and is operative to apply a spring-force to a second telescoping member of said plurality of telescoping members; wherein said first end member further comprises a second interconnection member that includes a seat portion extending laterally away from said tubular portion and sized to receive at least a portion of the first interconnection member, and said first interconnection member is defined by an eyelet tab and said seat portion is defined by an eyelet seat contoured to receive the eyelet tab.

11. An orthodontic appliance as recited in claim 10, wherein said first telescoping member and said end member are selectively interconnectable by axial advancement of said first interconnection member of the first telescoping member along said slot and rotational movement of said first interconnection member into said seat portion, and wherein said first telescoping member and said end member are selectively disconnectable by rotational movement of said first interconnection member out of said seat portion and axial retraction of said first interconnection member of the first telescoping member along said slot.

12. An orthodontic appliance as recited in claim 10, wherein aligned openings extend through each of said eyelet tab and said eyelet seat when said end member is interconnected to said end of the first telescoping member.

13. An orthodontic appliance as recited in claim 12, wherein said eyelet tab opening is offset from a center axis of said plurality of telescoping members.

14. An orthodontic appliance as recited in claim 13, further comprising:
  another eyelet tab at the other one of said opposing ends of the telescoping assembly, said another eyelet tab having an opening extending therethrough.

15. An orthodontic appliance as recited in claim 14, wherein said opening of said another eyelet tab is aligned with the center axis of the said plurality of telescoping members.

16. An orthodontic appliance as recited in claim 10, further comprising:
  an anchor member interconnectable to at least one of a mandibular arch or a maxillary arch, said first interconnection member being adapted for selective interconnection to and disconnection from said anchor member.

17. An orthodontic appliance as recited in claim 16, said interconnection member being adapted for selective interconnection to and disconnection from said anchor member in tandem with said second interconnection member.

18. An orthodontic appliance as recited in claim 16, said anchor member being adapted for selective interconnection to and disconnection from an orthodontic archwire.

19. A method for providing an orthodontic appliance for adjusting the relative positions of mandibular and maxillary arches, comprising:
  providing a telescoping assembly having a plurality of telescoping members said telescoping assembly having an interconnection member extending laterally from a first telescoping member of said plurality of telescoping members;
  interconnecting a first end member to an end of said telescoping assembly, said first end member including a tubular portion having a sidewall with a slot extending from an open end of the tubular portion along a length thereof and said first end member having a second interconnection member extending laterally from said tubular portion wherein said first end member is slidably advanced relative to the telescoping assembly during the first interconnecting step, and wherein upon interconnection of said first end member and said telescoping assembly a first spring member supportably retained by said first end member extends into an open end of the telescoping assembly and is operative to apply a spring-force to at least one of said plurality of said telescoping members;
  advancing said interconnection member through said slot along an axis of said end member;
  rotating one of said end member and said telescoping assembly to locate at least a portion of said interconnection member within a notched portion of said slot; and
  positioning at least a portion of the first interconnection member within a seat portion defined by said second interconnection member.

20. A method as recited in claim 19, further comprising:
  interchanging said first end member with a second end member, said interchanging step including:
  disconnecting said first end member from said telescoping assembly, wherein the first end member is slidably retracted relative to the telescoping assembly during the disconnecting step; and
  subsequently interconnecting said second end member to the end of the telescoping assembly, wherein said second end member is slidably advanced relative to the telescoping assembly during the second interconnecting step, wherein upon interconnection of said second end member and said telescoping assembly a second spring member supportably retained by said second end member extends into an open end of the telescoping assembly and is operative to apply a spring-force to at least one of said plurality of said telescoping members.

21. A method as recited in claim 20, wherein said second spring member and said first spring member have different spring attributes.

22. An orthodontic appliance for adjusting the relative positions of teeth comprising mandibular and maxillary arches comprising: a telescoping assembly having two opposing ends and a plurality of telescoping members including a first telescoping member having a first interconnection member extending laterally away therefrom; a first end member supportably retaining at least a portion of a first spring member, said first end member having a tubular portion with a slot extending through a sidewall thereof from an open end of the tubular portion along a length thereof, wherein said slot is sized for passage of the first interconnection member therethrough during selective interconnection and disconnection of the first telescoping member and the first end member, said first end member being adapted to slidably receive an end of the first telescoping member at one of said opposing ends for selective interconnection and disconnection therebetween, wherein when said first end member is interconnected to said end of the first telescoping member said first spring member extends into an open end of the first telescoping member and is operative to apply a spring-force to a second telescoping member of said plurality of telescoping members; and a retention notch extending from the slot through the tubular portion of the end member, the retention notch engages the first interconnection member and restricts relative axial movement of the first interconnection member and the first end member; wherein said first telescoping member and said first end member are selectively interconnectable by axial advancement of said first interconnection member of the first telescoping member along said slot and rotational movement of said first interconnection member into said retention notch, and wherein said first telescoping member and said first end member are selectively disconnectable by rotational movement of said first interconnection member out of said retention notch and axial retraction of said first interconnection member of the first telescoping member along said slot.

23. An orthodontic appliance as recited in claim 22, said first end member comprising:
   a tubular portion, wherein said first spring member is at least partially disposed within said tubular portion.

24. An orthodontic appliance as recited in claim 23, said tubular portion comprising:
   an open end and a closed end, wherein a first end of said first spring member is interconnected to said end member at said closed end of the tubular portion thereof, and wherein said spring member extends away from said closed end within said tubular portion.

25. An orthodontic appliance as recited in claim 22, further comprising:
   a second end member supportably retaining at least a portion of a second spring member, said second end member being adapted to slidably receive the end of the first telescoping member at one of said opposing ends for selective interconnection and disconnection therebetween, wherein when said second end member is interconnected to said end of the first telescoping member said second spring member extends into an open end of the first telescoping member and is operative to apply a spring-force to the second telescoping member, and wherein said first spring member and said second spring member have different spring attributes wherein the first end member and the second end member are selectively and fixedly securable to the first telescoping member.

26. An orthodontic appliance as recited in claim 25, wherein said first end member comprises a tubular portion and said second end member comprises a tubular portion, wherein said tubular portion of the first end member and the tubular portion of the second end member are of a substantially common configuration.

* * * * *

UNITED STATES PATENT AND TRADEMARK OFFICE
CERTIFICATE OF CORRECTION

PATENT NO.            : 9,237,941 B2
APPLICATION NO.       : 13/713963
DATED                 : January 19, 2016
INVENTOR(S)           : Andrew Hayes It is certified that error appears in the above-identified patent and that said Letters Patent is hereby corrected as shown below:

In claim 3, at column 18, line 16, there should be a hard return after the word "comprising:".

In claim 10, at column 18, line 55, there should be a hard return after the word "comprising:".

In claim 10, at column 18, line 58, there should be a hard return after the word "and".

In claim 10, at column 19, line 7, there should be a hard return after the word "members;".

In claim 22, at column 20, line 39, there should be a hard return after the word "comprising:".

In claim 22, at column 20, line 42, there should be a hard return after the word "therefrom;".

In claim 22, at column 20, line 57, there should be a hard return after the word "and".

In claim 22, at column 20, line 62, there should be a hard return after the word "member;".

Signed and Sealed this
Third Day of May, 2016

Michelle K. Lee
*Director of the United States Patent and Trademark Office*